United States Patent [19]

Braden et al.

[11] 4,251,462
[45] Feb. 17, 1981

[54] AMINOMETHYL CYCLODODECANES, A PROCESS FOR THEIR PRODUCTION AND THEIR USE AS CORROSION INHIBITORS

[75] Inventors: Rudolf Braden, Odenthal; Kuno Wagner, Leverkusen, both of Fed. Rep. of Germany

[73] Assignee: Bayer Aktiengesellschaft, Bayerwerk, Fed. Rep. of Germany

[21] Appl. No.: 69,700

[22] Filed: Aug. 27, 1979

[30] Foreign Application Priority Data

Sep. 6, 1978 [DE]   Fed. Rep. of Germany ....... 2838755

[51] Int. Cl.$^3$ .............................................. C07C 83/00
[52] U.S. Cl. ................................................... 564/455
[58] Field of Search ................................... 260/563 R

[56] References Cited

U.S. PATENT DOCUMENTS

| | | | |
|---|---|---|---|
| 3,312,742 | 4/1967 | Schneider et al. | 260/598 |
| 3,347,918 | 10/1967 | Schuster et al. | 260/563 R |
| 3,354,229 | 11/1967 | Cull et al. | 260/617 |
| 3,455,991 | 7/1969 | Bonnet | 260/563 R X |
| 3,758,527 | 9/1973 | Marxer | 260/563 R X |
| 3,873,621 | 3/1975 | Kreevoy et al. | 260/563 R X |

FOREIGN PATENT DOCUMENTS 1161147  8/1969  United Kingdom ................ 260/563 R

*Primary Examiner*—Paul F. Shaver
*Attorney, Agent, or Firm*—Gene Harsh; Joseph C. Gil; R. Brent Olson

[57] ABSTRACT

The instant invention is directed to aminomethyl cyclododecanes selected from the group consisting of aminomethyl cyclododecanes, bis-(aminomethyl)-cyclododecanes, tris-(aminomethyl)-cyclododecanes and mixtures thereof. The invention is also directed to a process for producing aminomethyl cyclododecanes, bis-(aminomethyl)-cyclododecanes, tris-(aminomethyl)-cyclododecanes, and mixtures thereof comprising reacting cyclododeca-1,5,9-triene with carbon monoxide and hydrogen in the presence of a rhodium-containing catalyst at temperatures of from 80° to 180° C. and under pressures of from 30 to 900 bars, separating the catalyst off from the hydroformylation product and treating the hydroformylation products with hydrogen at from 50° to 150° C. in the presence of ammonia and a hydrogenation catalyst, optionally after separating by distillation into the individual components.

12 Claims, No Drawings

AMINOMETHYL CYCLODODECANES, A PROCESS FOR THEIR PRODUCTION AND THEIR USE AS CORROSION INHIBITORS

BACKGROUND OF THE INVENTION

This invention relates to aminomethyl cyclododecanes selected from the group consisting of aminomethyl cyclododecane, bis-(aminomethyl)-cyclododecanes, tris-(aminomethyl)-cyclododecanes and mixtures thereof.

The present invention also relates to a process for producing these new compounds which is characterized in that cyclododeca-1,5,9-triene is reacted with carbon monoxide and hydrogen in the presence of a rhodium-containing catalyst at temperatures of from 80° to 180° C. and under pressures of from 30 to 900 bars. The catalyst is separated from the hydroformylation product and the hydroformylation products are treated with hydrogen in the presence of ammonia and a hydrogenation catalyst at from 50° to 150° C., optionally after separation by distillation into the individual components.

The present invention also relates to the use of the new compounds as corrosion inhibitors in heating oils, lubricants or motor fuels based on hydrocarbons.

The hydroformylation of cyclododeca-1,5,9-triene is known (U.S. Pat. Nos. 3,312,742 and 3,354,229; French Pat. No. 1,411,448 or British Pat. No. 1,161,147). According to these patents, corresponding $C_{13}$-alcohols and mixtures containing formyl cyclodocane in addition to formyl cyclodecene, formyl cyclodocadiene and the $C_{13}$-alcohol can be produced from cyclododecatriene using cobalt catalysts. Even under controlled conditions, the yield of formyl cyclododecane does not exceed 40% of the theoretical. Hydroxymethyl cyclododecanes are always obtained as the main product. Even under conditions under which formyl cyclooctane is obtained in a 56.7% yield from cycloocta-1,5-diene, hydroxymethyl cyclododecane is almost exclusively formed from cyclododeca-1,5,9-triene.

The production of di- and tri-formyl cyclododecanes would appear to involve even greater difficulties.

The use of cobalt complexes with trialkyl phosphite ligands in the hydroformylation of cyclododecatriene also results primarily in the formation of hydroxymethyl cyclododecane.

DESCRIPTION OF THE INVENTION

It has now been found that aminomethyl cyclododecanes containing from 13 to 15 carbon atoms, which may be represented by general formula (2) below

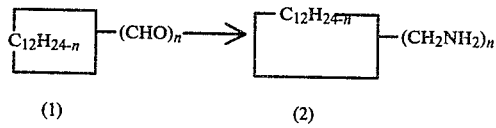

in which n is an integer of from 1 to 3, can be produced by reacting cyclododeca-1,5,9-triene with a mixture of carbon monoxide and hydrogen in the presence of a rhodium-containing and, optionally, cobalt-containing hydroformylation catalyst, which contains ligands having P, N or S as a hetero atom, at temperatures of from 80° to 180° C. and under pressures of from 30 to 900 bars. The resulting formyl cyclododecanes corresponding to general formula (1), in which n is an integer of from 1 to 3, is separated from the reaction mixture, particularly from the hydroformylation catalyst. The formyl cyclododecanes are then subjected to reductive amination with an excess of ammonia in the presence of a hydrogenation catalyst at from 50° to 150° C. and under a hydrogen pressure of from 10 to 200 bars. The reductive amination step may be optionally preceded by purification of the formyl cyclododecanes present in the reaction mixture by distillation. It is possible particularly in the optional production of compounds containing at least 2 amino groups, to separate the monofunctional formyl cyclododecane by distillation before the reductive amination step and optionally to subject it separately to reductive amination.

The cyclododecatriene used as a starting material is known. It may be obtained, for example, by trimerizing butadiene with metal catalysts, as described in Angewandte Chemie, Vol. 69, page 397 (1957). The cyclododeca-1,5,9-triene may be used in the cis-trans-trans- and in the trans-trans-trans-configuration.

To carry out the hydroformylation reaction, carbon monoxide and hydrogen are generally used in an at least stoichiometric ratio, but advantageously in excess, for example, up to 1,000 mol %. The mixture of carbon monoxide and hydrogen contains carbon monoxide and hydrogen in a ratio by volume of generally from 1:4 to 4:1 and more particularly from 2:1 to 1:2.

Hydroformylation is carried out at a temperature in the range of from 80° to 180° C. Temperatures in the range of from 90° to 165° C. have proved to be particularly suitable. In addition, a pressure of from 30 to 900 bars is maintained during the reaction. It is advantageous to apply a pressure in the range of from 200 to 400 bars. The reaction temperature is adjusted according to the required reaction product. Thus, the monoaldehyde from which the monoamine is produced is preferentially formed at temperatures in the range of from 80° to 120° C., while the tris-formyl cyclododecane is preferentially formed at temperatures above 150° C. The reaction time is dependent upon the reaction temperature. To obtain the tris-formyl cyclododecane, the concentration of cyclododecatriene in the reaction mixture has to be kept low by slowly introducing the triene into the reaction mixture.

Suitable hydroformylation catalysts are rhodium complexes with one or more nitrogen-, phosphorus- and/or sulfur-containing ligands. Preferred rhodium complexes used as catalysts have the formulae:

$XRh(CO)L_2$, $XRh(CO)L_3$, $RhXL_3$, $[Rh(CO)_2L_2]_2$, $[Rh(OCOCH_3)—(CO)L]_2$ where X is a chlorine, bromine or iodine atom and L is an organic ligand. Suitable organic ligands are tertiary organic phosphines, phosphites, dialkyl sulfides and tertiary amines. Suitable ligands are, for example, tertiary organic phosphines or organic phosphites containing as organic radicals identical or different $C_1$–$C_{20}$-alkyl radicals, $C_5$-$C_{12}$-cycloalkyl radicals, $C_7$–$C_{10}$-aralkyl radicals and at least one $C_6$–$C_{10}$-aryl radical. The abovementioned radicals may contain substituents which are inert under the reaction conditions. Examples include from 1 to 2 hydroxyl groups, $C_1$–$C_4$-alkoxy or carboalkoxy groups, amino groups or halogen atoms, such as triphenyl phosphine, diethyl phenyl phosphine, tritolyl phosphine, trinaphthyl phosphine, diphenyl methyl phosphine, diphenyl butyl phosphine, tris-(p-chlorophenyl)-phosphine, tris-(p-carbomethoxyphenyl)-phosphine, tris-(p-cyanophenyl)-phosphine, diphenyl phosphonous acid phenyl ester, benzene phosphonous acid diphenyl ester and triphenyl phosphite, P[CH$_2$CH$_2$CH$_2$N(CH$_3$)$_2$]$_3$,
P[CH$_2$CH$_2$CH$_2$N(C$_2$H$_5$)$_2$]$_3$,

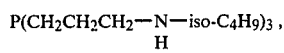

P[CH$_2$CH$_2$CH$_2$N(iso—C$_4$H$_9$)$_2$]$_3$,
(n—C$_4$H$_9$)$_2$PCH$_2$CH$_2$N(C$_2$H$_5$)$_2$,
P[CH$_2$N(C$_2$H$_5$)$_2$]$_3$,
P[C$_6$H$_4$N(CH$_3$)$_2$]$_3$,
P[CH$_2$CH$_2$C$_6$H$_4$N(C$_2$H$_5$)$_2$]$_3$,

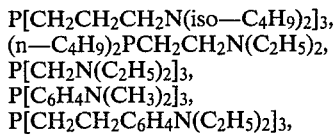

P[CH$_2$CH$_2$CH$_2$N(ter.C$_4$H$_9$)$_2$]$_3$ and
P[CH$_2$CH$_2$CH$_2$N(iso—C$_3$H$_7$)$_2$]$_3$.

The phosphorus-containing ligands used are preferably triaryl phosphines, triaryl phosphites and triaryl phosphates. The triaryl phosphines and triaryl phosphites are normally the most suitable. It is also possible in accordance with the present invention to use complex ligands in the form of triorganophosphines partially substituted by ferrocene (cf. German Offenlegungsschrift No. 2,617,306). In general, however, it is possible to use any triorganophosphorus ligand which is known to be suitable for rhodium-catalyzed hydroformylation reaction systems.

Suitable nitrogen-containing ligands are, for example, pyridine, picolines, ethyl pyridines, N-methyl pyrrolidine, N-methyl pyrrole, N,N′-dimethyl piperazine, dimethyl cyclohexylamine, triethylamine, N,N-dimethyl aniline, N-methyl morpholine, N-methyl indole, quinoline, isoquinoline, N-methyl pyrrolidone and 3-dimethylaminonproprionitrile.

Suitable sulfur-containing ligands are, for example, dibenzyl sulfide, di-n-butyl sulfide, dimethyl sulfoxide, diethyl sulfide, di-(4-chlorobenzyl)-sulfide, di-(4-cyanobenzyl)-sulfide, bis-(4-dimethylaminobenzyl)-sulfide, di-(4-diethylaminobenzyl)-sulfide, di-(α-naphthylmethyl)-sulfide, di-(2,6-dichlorobenzyl)-sulfide, di-(3,4-dichlorobenzyl)-sulfide, di-(2-chlorobenzyl)-sulfide, di-(5,6,7,8-tetrahydronaphthyl-2-methyl)-sulfide, benzyl methyl sulfide, benzyl dodecyl sulfide, 4-dimethylaminobenzyl methyl sulfide, benzyl butyl sulfide, bis-(4-carboxybenzyl)-sulfide, di-(4-methylbenzyl)-sulfide, di-(3-methylbenzyl)-sulfide and di-(2-methylbenzyl)-sulfide.

The method by which the catalytic complex of the rhodium with the ligand and carbon monoxide is introduced into the hydroformylation reaction system is not important. The quantitative ratio of the ligand to the rhodium in the catalyst complex may lie within a wide range. The liquid reaction medium normally contains, however, at least about 1 mol of the ligand (for example triphenylphosphine) per gram atom of rhodium. The ligand may also, however, be added in a large excess.

It is possible to replace some of the rhodium in the catalyst system by cobalt.

In the reaction of the cyclododecatriene with carbon monoxide and hydrogen, the rhodium catalyst is used in a quantity corresponding to between 1 and 1,000 mg of rhodium metal per kg of cyclododecatriene. Where cobalt is additionally used as a catalyst, the quantity of rhodium used may be reduced to between one tenth and one hundredth mg. Cobalt is used in a quantity corresponding to between 0.1 and 10 g of cobalt per kg of cyclododecatriene.

In particular, from 10 to 600 mg of rhodium are used per kg of cyclododecatriene. The catalyst may be recovered by known methods and reused.

Hydroformylation is carried out in the liquid phase. It is possible to fix the homogeneous catalyst to a solid support, as described by P. I. Davidson et al in Catalysis, Vol. 1 (1976), pages 391–393.

The liquid reaction medium may be either a mixture of liquids present per se (i.e. reaction products, excess ligand, etc.) or even an added solvent which is inert under the reaction conditions and in which the homogeneous catalyst and the excess ligand are soluble. Unless a separate solvent is used, the reaction medium generally contains an excess of the ligand (for example, triphenyl phosphine) and reaction products including, in particular, those secondary products which are less volatile than the carbonyl reaction product itself.

In cases where the reaction is carried out in the presence of a separately added solvent, it is possible to use a variety of different inert liquids, for example alkyl-substituted benzenes, pyridine or alkyl-substituted pyridines, tertiary amines, highboiling esters (such as dialkyl, dicarboxylates, triorganophosphates or esters of polyols, such as trimethylol propane or pentaerythritol), ketones, alcohols (such as the butanols), nitriles (such as acetonitrile), or hydrocarbons (such as saturated aliphatic or cycloaliphatic hydrocarbons).

It is preferred to use solvents of the type which may also be used for the reductive amination step, such as benzene, toluene, xylene, isopropanol, methyl cyclohexane, decalin, dioxane, tetrahydrofuran, ethylene glycol monoethyl ether or diethylene glycol dimethyl ether.

The aldehydes obtained by hydroformylation may be separated off from the catalyst by a known method, for example by distillation, and subsequently subjected to the reductive amination step. In many cases in the production of pure monoamines or in the production of polyamines free from monoamines, it is advisable to split up the hydroformylation product into the corresponding components by distillation before the reductive amination step. It is also possible to subject the mixture of hydroformylation products to reductive amination and then to separate monoamines and polyamines by distillation. The solvent optionally used for hydroformylation may also be used for the reductive amination step. Reductive amination is carried out in the presence of a hydrogenation catalyst and at least 3 mols of ammonia per mol of the formyl cyclododecane. It is also possible to carry out reductive amination in the absence of a solvent or in the aminomethyl cyclododecanes according to the present invention or in a large excess of ammonia. A molar ratio of ammonia to formyl compound of more than 10:1 is preferred. It can be advantageous to add catalytic quantities of an acid. It is preferred to add from 0.1 to 3%, by weight, of phosphoric acid, propionic acid or succinic acid.

Reductive amination is carried out at temperatures of from 50° to 150° C. and, more preferably, at temperatures of from 90° to 135° C. The hydrogen pressure should amount to more than 10 bars and, more particularly, to between 50 and 200 bars.

Suitable reductive amination catalysts are hydrogenation catalysts containing as an active component metals having atomic numbers of from 23 to 29 in metallic and/or oxidic form. Suitable catalysts are, for example, nickel or cobalt catalysts, such as nickel on a support. Suitable supports include inorganic materials, such as kieselguhr, silicas, aluminum oxides, silicas, aluminum silicates, montmorillonite, zeolites, spinels, dolomite, kaolin, magnesium silicates, zirconium oxide, iron oxide, zinc oxide, calcium carbonate, silicon carbide, aluminum phosphate, boron phosphate, asbestos or active carbon. Suitable supports also include organic materials in the form of naturally occurring or synthetic compounds of high molecular weight, such as silk, polyamides, polystyrenes, cellulose or polyurethanes. The supports may be used in the form of beads, strands, filaments, cylinders, polygons or in powder form. Raney-type catalysts, such as Raney nickel, W-1-, W-5-, W-6-, W-7-Raney nickel, as described by H. Adkins, in J.Am.-Chem. Soc. 69, 3039 (1974), Raney cobalt catalysts, Raney copper, Raney nickel-iron, Raney cobalt-nickel, Raney cobalt-iron; metal catalysts produced by the reduction of nickel or cobalt salts (such as Urushibara nickel) or nickel or cobalt salts reduced with metal alkyl compounds, alkali hydrides, hydrazine, boronates or boron hydride; catalysts produced by the reduction of metal oxides or metal oxide mixtures; or metal oxide or metal oxide mixtures may also be used.

The metal oxides or metal salts may even be reduced using hydrogen, optionally at elevated temperature and elevated pressure or under the conditions of the process or during the process.

The catalysts may contain one or more of the following elements in quantities of up to 10% as accelerators: Li, Na, Ca, Ba, K, Ag, Be, La, Ce, Ti, V, Nb, Ta, Mo, W and up to 1% of the elements Ru, Rh, Pd, Au, Ir, Pt.

Particularly preferred hydrogenation catalysts are Raney catalysts, such as Raney nickel, Raney cobalt and Raney nickel-iron.

For producing diamino and triaminomethyl compounds, it can be advantageous initially to introduce the catalyst, ammonia and a solvent or the end product into a hydrogenation autoclave under hydrogen pressure, at the hydrogenation temperature and to pump in the corresponding formyl cyclododecane, optionally in a solvent.

The amines according to the present invention may be separated off from the reaction mixture by distillation after the hydrogenation catalyst has been removed by a known method, for example, by filtration or centrifuging.

The amines according to the present invention are aminomethyl-substituted cyclododecanes containing from 1 to 3 aminomethyl substituents per molecule. Unless the hydroformylation products used as an intermediate stage are split up into their components, the end products according to the invention are generally obtained in the form of a mixture containing monoamines, diamines and triamines. The content of monoamines, diamines and triamines may be adjusted within certain limits, for example, by correspondingly selecting the hydroformylation temperature. Monoamines, diamines and triamines or mixtures exclusively containing diamines and triamines may be purified by correspondingly subjecting the intermediate stage of the hydroformylation product to purification by distillation because the composition of the end products according to the invention corresponds to the composition of this intermediate stage. It is also possible, however, to split up the reaction mixture into its individual components on completion of reductive amination, for example, by distillation. The diamines and triamines according to the present invention are isomer mixtures whose exact composition has no bearing on the described uses of the amines according to the invention.

The amines according to the present invention are valuable corrosion inhibitors which, by virtue of their high hydrocarbon content, show in particular a high level of compatibility with heating oils, lubricants and hydrocarbon-based motor fuels. In addition, the diamines and triamines according to the invention and their mixtures may be used as crosslinking agents and chain extenders for epoxide resins and NCO-prepolymers of the type used in known methods for the production of polyurethane polyureas.

EXAMPLES

EXAMPLE 1

Hydroformylation of cyclododecatriene

The catalyst, 75 mg of tris-(dibenzyl sulfide)-tris-chloro-rhodium and 2.4 g of dicobalt octacarbonyl, and 500 g of toluene are introduced into a fine-steel autoclave. The autoclave is repeatedly purged with a 1:1 gas mixture of carbon monoxide and hydrogen with which a pressure of up to 100 bars is established. The autoclave is heated with stirring to 170° C. and the pressure is increased to 200 bars using the same gas mixture, the pressure subsequently being kept constant by the introduction of more CO/H$_2$ when the pressure falls. After 1 hour, the temperature is reduced to 110° C. and a solution of 500 g of cyclododeca-1,5,9-triene in 1,000 g of toluene is pumped into the autoclave over a period of 3 hours. After another 90 minutes, the reaction mixture is cooled and the autoclave is vented and purged with nitrogen. The reaction solution is filtered. The solvent is distilled off at 1,600 Pa. The reaction product is distilled in a thin layer evaporator at 13 Pa and at a jacket temperature of around 220° C. The composition of the distillate is determined by gas chromatography (column: 1 m Carbowax 6000 on Teflon; heating rate: 15° C./min; 130° to 260° C.). The sample is diluted with tetrahydrofuran.

Table 1 below shows the results of the tests of Examples 1 to 6 which were carried out in the same way as described in Example 1, but using the catalyst and solvents and under the reaction conditions (reaction time and temperature) indicated in Table 1.

Redistillation of the thin-layer-distilled reaction mixture of Example 2 gave bis-formyl cyclododecane in a purity of approximately 95%, boiling point: 102° C. at 0.7 Pa C$_{14}$H$_{24}$O$_2$, molecular weight 224.3

Redistillation of the reaction mixture of Example 6 gave the monoformyl cyclododecane in a purity of more than 95%; boiling point: 91° to 93° C. at 13 Pa, n$_D^{20}$ 1.4853.

TABLE 1

| Example No. | 1 | 2 | 3 | 4 | 5 | 6 |
|---|---|---|---|---|---|---|
| Catalyst | | | | | | |
| ligand L | | ($\phi$CH$_2$)$_2$S$\phi_3$P | $\phi_3$P | ($\phi$CH$_2$)$_3$N | ($\phi$CH$_2$)$_2$S | $\phi_3$P |

TABLE 1-continued

| Example No. | 1 | 2 | 3 | 4 | 5 | 6 |
|---|---|---|---|---|---|---|
| g Rh/kg cyclododecatriene | 0.018 | 0.2 | 0.5 | 0.2 | 0.012 | 0.5 |
| gCo/kg cyclodecatriene | 0.1 | — | — | — | 0.7 | — |
| molar ratio L/Rh | 3 | 6 | 6 | 3 | 3 | 6 |
| solvent | toluene | toluene | dioxane | THF** | toluene | toluene |
| Reaction Conditions | | | | | | |
| temperature °C. | 110 | 120 | 160 | 160 | 130 | 100 |
| pressure bars | 200 | 300 | 300 | 200 | 200 | 150 |
| pumping-in time in hours | 3 | 3 | 5 | 2 | 3 | 2 |
| total reaction time in hours | 4.5 | 4 | 6 | 3 | 4 | 3 |
| Conversion in % | | | | | | |
| Yield in mol % | | | | | | |
| monoformyl-CD*** | 13.9 | 9.2 | 0.1 | 43.1 | 46.0 | 59.5 |
| bisformyl-CD | 57.7 | 71.8 | 13.1 | 4.9 | 21.2 | 19.1 |
| triformyl-CD | 26.2 | 13.0 | 85.5 | — | 2.0 | — |
| residue in % | 2.8 | 5.0 | — | 3.7 | 1.6 | 2.8 |

*φ = $C_6H_5$—;
**tetrahydrofuran;
***CD = cyclododecane

REDUCTIVE AMINATION

EXAMPLE 7

Aminomethyl cyclododecane 235 g of formyl cyclododecane, 2 g of acetic acid, 250 g of tetrahydrofuran and 20 g of Raney cobalt are introduced into a fine-steel stirrer-equipped autoclave. The autoclave is closed and purged with nitrogen. 300 g of liquid ammonia are pumped into the autoclave. The contents of the autoclave are then heated to 110° C. under a hydrogen pressure of 80 bars, after which the pressure (up to 120 bars) is kept constant using hydrogen for 45 minutes. Reductive amination is then over. After the ammonia has been evaporated, the catalyst is removed from the cooled reaction mixture by filtration and the solvent distilled off. Distillation at 13 Pa gives a fraction boiling at from 112° to 113° C. of which up to 98.5% consists of aminomethyl cyclododecane. $n_D^{20}$ 1.5012, val: observed 200 (theoretical 197), yield: 86.7%.

EXAMPLE 8

50 g of Raney nickel, 1,000 g of methanol and 2 g of phosphoric acid are introduced into an autoclave. After the autoclave has been closed and purged with nitrogen, 700 g of ammonia are introduced. The autoclave is then heated to 95° C. under hydrogen pressure so that a pressure of 120 bars is established. At 90° to 100° C./120 bars pressure (the pressure is kept constant by the introduction of more nitrogen), a solution of 500 g of a mixture emanating from the formylation of cyclododeca-1,3,5-triene and containing 7.9%, by weight, of monoformyl cyclododecane, 71.6%, by weight, of bisformyl cyclododecane and 14.7%, by weight, of trisformyl cyclododecane in 1,000 g of methanol is pumped in over a period of 90 minutes. The contents of the autoclave are then stirred for 10 minutes at 105° C./120 bars.

Working up of the reaction mixture in the usual way gave 435 g of an amine mixture which distilled over in a thin-layer evaporator at 25 Pa and at a wall temperature of 170° C. According to its gas chromatogram, this mixture contained 8.5% of mono-, 76.3% of di- and 13.4% of tri-(aminomethyl)-cyclododecane.

It is possible by redistilling this mixture to obtain a fraction boiling at 122°–140° C./1.3 Pa which, in addition to 41% of di-(aminomethyl)-cyclododecane, contains approximately 59% of tri-(aminomethyl)-cyclododecane and is free from mono-(aminomethyl)-cyclododecane.

The di-(aminomethyl)-cyclododecane (purity 99%) boils at 108° C./1.3 Pa; $n_D^{20}$ 1.5163.

What is claimed is:

1. Aminomethyl cyclododecanes selected from the group consisting of aminomethyl cyclododecanes, bis-(aminomethyl)-cyclododecanes, tris-(aminomethyl)-cyclododecanes and mixtures thereof.

2. A process for producing aminomethyl cyclododecanes, bis-(aminomethyl)-cyclododecanes, tris-(aminomethyl)-cyclododecanes, and mixtures thereof comprising reacting cyclododeca-1,5,9-triene with carbon monoxide and hydrogen in the presence of a rhodium-containing catalyst at temperatures of from 80° to 180° C. and under pressures of from 30 to 900 bars, separating the catalyst off from the hydroformylation product and treating the hydroformylation products with hydrogen at from 50° to 150° C. in the presence of ammonia and a hydrogenation catalyst, optionally after separating by distillation into the individual components.

3. The process of claim 2, wherein the volume ratio of carbon monoxide to hydrogen is 1:4 to 4:1.

4. The process of claim 3, wherein the volume ratio is 2:1 to 1:2.

5. The process of claim 2, wherein the hydroformylation is carried out at 90° to 165° C. and 200 to 400 bars pressure.

6. The process of claim 2, wherein said rhodium-containing catalyst is of the formulae:
   $XRh(CO)L_2$, $XRh(CO)L_3$, $RhXL_3$, $[Rh(CO)_2L_2]_2$, $[Rh(OCOCH_3)-(CO)L]_2$
wherein
   X is chlorine, bromine or iodine and
   L is an organic ligand.

7. The process of claim 6, wherein said rhodium-containing catalyst is tris-(dibenzyl sulfide)-tris chlororhodium.

8. The process of claim 2, wherein 1–1,000 mg of rhodium metal is used per kg of cyclododeca-1,5,9-triene.

9. The process of claim 8, wherein cobalt is used as a co-catalyst and said rhodium may be reduced to between 0.1 and 0.01 mg.

10. The process of claim 2, wherein the hydroformylation is carried out in the presence of solvent.

11. The process of claim 2, wherein said hydrogenation catalyst has as an active component metals having atomic numbers of from 23 to 29 in metallic and/or oxidic form.

12. The process of claim 11, wherein said hydrogenation catalysts are Raney catalysts.

* * * * *